United States Patent [19]

Beale

[11] Patent Number: 5,756,469
[45] Date of Patent: May 26, 1998

[54] COMPOSITION OF PYRUVATE AND ANTI-CORTISOL COMPOUNDS AND METHOD FOR INCREASING PROTEIN CONCENTRATION IN A MAMMAL

[76] Inventor: Paxton K. Beale, 1801 Bush St., Suite 300, San Francisco, Calif. 94109

[21] Appl. No.: 686,820

[22] Filed: Jul. 26, 1996

[51] Int. Cl.$^6$ .................. A61K 31/70; A61K 31/715; A61K 31/685
[52] U.S. Cl. .................. 514/23; 514/53; 514/78
[58] Field of Search .................. 514/23, 53, 78

[56] References Cited

U.S. PATENT DOCUMENTS

| | | | |
|---|---|---|---|
| 4,351,835 | 9/1982 | Stanko | 424/252 |
| 4,415,576 | 11/1983 | Stanko | 424/252 |
| 4,548,937 | 10/1985 | Stanko | 514/251 |
| 4,645,764 | 2/1987 | Stanko | 514/251 |
| 4,812,479 | 3/1989 | Stanko | 514/557 |
| 4,874,790 | 10/1989 | Stanko | 514/557 |
| 4,981,687 | 1/1991 | Fregly et al. | 424/439 |
| 5,028,440 | 7/1991 | Nissen | 426/2 |
| 5,087,472 | 2/1992 | Nissen | 426/623 |
| 5,089,477 | 2/1992 | Fregly et al. | 514/23 |
| 5,134,162 | 7/1992 | Stanko | 514/557 |
| 5,147,650 | 9/1992 | Fregly et al. | 424/439 |
| 5,236,712 | 8/1993 | Fregly et al. | 424/439 |
| 5,238,684 | 8/1993 | Fregly et al. | 424/439 |
| 5,256,697 | 10/1993 | Miller et al. | 514/625 |
| 5,283,260 | 2/1994 | Miller et al. | 514/563 |
| 5,294,606 | 3/1994 | Hastings | 514/53 |
| 5,294,641 | 3/1994 | Stanko | 514/540 |
| 5,312,985 | 5/1994 | Dhaon et al. | 564/143 |
| 5,348,979 | 9/1994 | Nissen et al. | 514/557 |
| 5,360,613 | 11/1994 | Nissen | 424/439 |
| 5,428,072 | 6/1995 | Cook et al. | 514/560 |
| 5,430,066 | 7/1995 | Cook et al. | 514/558 |
| 5,472,980 | 12/1995 | Miller | 514/563 |
| 5,480,909 | 2/1996 | Stanko | 514/557 |
| 5,508,308 | 4/1996 | Miller et al. | 514/563 |
| 5,536,751 | 7/1996 | Bunger | 514/557 |

OTHER PUBLICATIONS

"Conjugated Linoleic Acid (CLA)", 1996 Supplement Review, 19–22, 1966.

Monteleone, et al., "Blunting by chronic phosphatidylserine administration of the stress–induced activation of the hypothalamo–pituitary–adrenal axis in healthy men", European Journal at Clinical Pharmacology, 1992.

Monteleone, et al., "Effects of Phosphatidylserine on the Neuroendocrine Response to Physical Stress in Humans", Neuroendocrinology, 1990; 52:243–248.

Nestler, et al. "Dehydroepiandrosterone Reduces Serum Low Density Lipoprotein Levels and Body Fat but Does not Alter Insulin Sensitivity in Normal Men", Journal of Clinical Endocrinology and Metabolism, vol. 66, No. 1:57–61, 1988.

Morales, et al., "Effects of Replacement Dose of Dehydroepianodrosterone in Men and Women of Advancing Age", Journal of Clinical Endocrinology and Metabolism, vol. 78, No. 6:1360–1367, 1994.

Kurzman, et al., "Reduction in Body Weight and Cholesterol in Spontaneously Obese Dogs By Dehydroepiandrosterone", International Journal of Obesity, 14:95–104, 1990.

Heymsfield, et al., "Chemical and elemental analysis of humans in vivo using improved body composition models", American Journal of Physiology, 261:E190–E198,1991.

Brunner, "HMB, KIC and Leucine—Anticatabolic Bodybuilding Nutrients From the Same Branched Chain", IM, 100–101, Jul. 1996.

Fritz, "Phosphatidylserine—Have We Found a Medically Proven Cortisol Antagonist at Last?", IM, 74–75, Feb. 1996.

Brunner, "Phosphatidylserine", IM, 68–70, Aug. 1996.

Block, "Amino Acid Handbook—Methods and Results of Protein Analysis".

"MLO—Gain Muscle & Lose Bodyfat—Hardbody—Muscle–Zyme / Questions & Answers", Pamphlet.

"MLO—Hardbody—Muscle–Zyme", Sample Product Label.

"First Strike—World's First Cortisol Blocker", Sales Aide.

"Atletika—Thriad Centered Training", Sales Brochure.

"Cortistat–PS", Advertisement.

"Develop Peak Performance Naturally—Corti–PS Sports Supplement", Sales Aide.

"Corti–PS–30P", Technical Data Sheet.

"Corti–PS–20P", Technical Data Sheet.

"Corti–PS–20F", Technical Data Sheet.

Memorandum regarding Corti–PS Phosphatidylserine (PS) dated Aug. 24, 1995.

Primary Examiner—Kevin E. Weddington
Attorney, Agent, or Firm—Donald O. Nickey; Standley & Gilcrest

[57] ABSTRACT

The present invention is based, in part, upon the discovery that the use of pyruvate in combination with a cortisol blocker, such as phosphatidylserine, produces a synergistic effect in increasing lean body mass or muscle tissue, decreasing fat deposition, increasing endurance and athletic performance of a mammal consuming same. The invention also relates to a method of treating the catabolic effects of diseases such as cancer and AIDS by the administration of pyruvate and a cortisol blocker.

The present invention also discloses a synergistic composition comprising pyruvate and a cortisol blocker. More specifically, the present invention relates to a composition which comprises pyruvate and/or derivatives of pyruvate and phosphatidylserine.

14 Claims, No Drawings

COMPOSITION OF PYRUVATE AND ANTI-CORTISOL COMPOUNDS AND METHOD FOR INCREASING PROTEIN CONCENTRATION IN A MAMMAL

TECHNICAL FIELD

The present invention relates generally to a composition for enhancing the protein concentration or muscle mass of a mammal and a method for enhancing the protein concentration or muscle mass in a mammal. More specifically, the present invention relates to a composition which comprises pyruvate and/or derivatives of pyruvate and an anti-cortisol or cortisol blocker compound. The method of the present invention comprises administering to a mammal in need of enhancing its protein concentration or muscle mass, a composition comprising pyruvate and an anti-cortisol compound.

BACKGROUND ART

Athletes engage in strenuous training to accomplish the goals of their sport. This strenuous training essentially amounts to trauma to the body, in that the human body interprets every strenuous work-out as a threat to its survival. It is known that muscle damage, caused by training, releases the catabolic hormone prostaglandin-E2. Training also causes the release of adrenocorticotropin (ACTH), which is a pituitary hormone. The presence of increased levels of ACTH increases the production of the catabolic hormone cortisol. Cortisol is also known as hydrocortisone, which is a glucocorticoid of the adrenal cortex that is a derivative of cortisone and is used in the treatment of rheumatoid arthritis. Thus, cortisol is a naturally occurring anti-inflammatory steroid. This catabolic hormone results in the release of amino acids from muscle tissue and prevents absorption of glucose. Cortisol, as a catabolic stress hormone, cannibalizes muscle tissue. High cortisol levels also result in the breakdown of connective tissue, lowered immunity and reduced muscle RNA synthesis. While cortisol may be a detriment to the athlete, scientists have conjectured that when the human body is stressed or traumatized, it triggers a "fight or flight" survival response. The biological design of cortisol is such that when a human is threatened, cortisol levels rise and mobilize the body for action by breaking down fat and muscle stores for emergency energy. Cortisol also reduces swelling in the event of injury. After the threat or trauma has subsided, cortisol levels return to normal. The cortisol-stress relationship is designed for intermittent physical threats and not the constant stimulation provided by today's aggressive athletes. Ongoing training results in cortisol levels that do not return to normal for extended periods of time and thereby result in the breakdown or loss of muscle tissue.

In order to reduce the catabolic effect of prolonged, intense training, a cortisol antagonist or blocker would be beneficial to the athlete. As used herein and in the claims, the term "cortisol blocker" means any known chemical entity that, when administered to an animal, will retard or prevent the production of cortisol or inhibit or prevent the catabolic activity of cortisol against muscle tissue.

Monteleoni et al., *European Journal of Clinical Pharmacology*, pages 385–388 (1992) investigated the chronic administration of phosphatidylserine derived from brain cortex on the neuroendocrine responses to physical stress. The Monteleoni study found that phosphatidylserine derived from brain cortex administered orally at 800 mgs per day for 10 days prior to exercise, significantly reduced the ACTH and cortisol responses to physical exercise. A 400 mg per day dose was shown by Monteleoni to produce no effect on the cortisol response. Phosphatidylserine is representative of a large class of neutral lipids. Phosphatidylserine is an essential component of biological membranes and occurs in the internal layer of the cell membrane.

In 1990, Monteleoni et al. reported in *Neuroendocrinology*, 1990; 52: pages 243–248, on the activity of brain cortex-derived phosphatidylserine on the neuroendocrine and neurovegetative responses to physical stress. In a double blind design, before starting the exercise, each human subject received intravenously the brain cortex derived phosphatidylserine or a placebo. Blood samples were collected before and after the exercise for plasma ACTH, cortisol and growth hormone. It was determined that physical stress induced an increase in ACTH, cortisol and growth hormone in the placebo group while the group receiving phosphatidylserine showed a reduced production of ACTH and cortisol.

β-hydroxy-β-methylbutyrate (HMB) is another compound known to increase lean-mass gains in weight trainers who consumed at least 3 grams per day. HMB is a leucine metabolite and it has been hypothesized from work in animal models that HMB decreases protein breakdown induced by resistance exercise, resulting in increased muscle mass and function.

U.S. Pat. No. 5,348,979 discloses a method of protein sparing, comprising orally or intravenously administering to a human β-hydroxy-β-methylbutyric acid (HMB). The '979 patent also teaches that the HMB can be in the free acid form, its mineral salts, esters or lactose derivatives. More specifically, the '979 patent discloses a method for improving the protein nutrition in elderly humans by administering HMB.

U.S. Pat. Nos. 5,360,613; 5,028,440 and 5,087,472 disclose and claim the administration of HMB to humans and meat producing domestic animals for treating elevated blood levels of low density lipoprotein cholesterol and total cholesterol, for increasing lean tissue development and for use as a feed additive. The teachings of U.S. Pat. Nos. 5,348,979; 5,360,613; 5,028,440 and 5,087,472 are herein incorporated by reference.

U.S. Pat. No. 4,981,687 discloses compositions and methods for achieving improved physiological response to exercise. More specifically, this patent teaches a beverage comprising water, sugar, electrolytes, glycerol and pyruvate; and its use to ameliorate the effects of physical exertion. The teachings of U.S. Pat. No. 4,981,687 are incorporated herein by reference.

U.S. Pat. No. 5,089,477 discloses the use of pyruvate in a liquid composition that is used to prevent weight loss in agricultural animals resulting from dehydration.

U.S. Pat. No. 5,147,650 and U.S. Pat. No. 5,238,684 discloses and claims a fluid composition comprising water, electrolytes, sugar, glycerol, lactate and pyruvate. The teachings of U.S. Pat. Nos. 5,147,650 and 5,238,684 are incorporated herein by reference.

U.S. Pat. No. 5,236,712 discloses and claims a beverage containing water, electrolytes, pyruvate and alanine in a concentration of from about 0.5% to about 10%. The teachings of U.S. Pat. No. 5,236,712 are incorporated herein by reference.

Dehydroepiandrosterone (DHEA) is a naturally occurring hormone produced by the adrenal gland. The level of serum DHEA decreases in humans from the age of about 25. Studies in humans have indicated that this hormone has the ability to increase muscle strength, add lean body mass, induce body fat loss, prolong endurance and increase IGF-1. Studies have shown that dosages of DHEA as high as 1.6 gm/day are safe and without side effects.

Nestler et al., in the *Journal of Clinical Endocrinology and Metabolism*, Vol. 66, No. 1 (pages 57–61) reported a DHEA study wherein five men were given a placebo and five men were given 1600 mg/day of DHEA for 28 days in a randomized double blind study. The DHEA group evidenced a mean percent body fat decrease of 31% with no change in weight. DHEA subjects also evidenced a fall in mean serum total cholesterol levels.

Morales et al., in the *Journal of Clinical Endocrinology and Metabolism*, Vol. 78, No. 6 (pages 1360–1367), reported a DHEA study wherein a randomized placebo-controlled cross-over trial of 50 mg per day DHEA administration for 6 months was conducted. The conclusion of this study was that restoration of DHEA in age advanced humans induced an increase in bioavailable IGF-1, which, with time, may result in an improvement in anabolic processes and physical/psychological well-being.

Conjugated linoleic acid (CLA) is found in cheese, lamb meat and bovine muscle tissue. Dosages of effective amounts of CLA are not practical from normal nutrition due to its low levels of concentration in regular foods. CLA is also known to have antioxidant properties like those of vitamin E and β-carotene.

U.S. Pat. Nos. 5,430,066 and 5,428,072 to Cook et al. disclose and claim a method of enhancing weight gain and feed efficiency in an animal which comprises administration of a conjugated linoleic acid. More specifically, these patents relate to the enteral or parenteral administration of 9,11-octadecadienoic acid; 10,12-octadecadienoic acid or the non-toxic salts thereof to mammals to increase the efficiency of feed conversion. These patents also claim a method of preventing weight loss, reduction in weight gain or anorexia in an animal caused by immune stimulation of the animal by endotoxin through the administration of conjugated linoleic acid, free linoleic acid, salts thereof and mixtures thereof. Even more specifically, the '066 patent discloses and claims a method for alleviating the adverse effects produced by interleukin-1 through the administration of CLA. The teachings of U.S. Pat. Nos. 5,430,066 and 5,428,072 are herein incorporated by reference.

A further example of known cortisol blockers, the compound known as ipriflavone (7-isoproxy-isoflavone) is submitted. Ipriflavone is presently used in dosages of about 600 mgs per day to treat women suffering from osteoporosis. Ipriflavone is known to have an anabolic effect on meat producing domestic animals. Human studies with an administration rate of 20 mg/kg/day of body weight, evidenced an increase in body weight of about 5 pounds (2 kg) in four weeks without an increase in caloric intake. Ipriflavone is also known to increase athletic endurance, suppress the catabolic effect of cortisone and conserve nitrogen in skeletal muscle.

Creatine monohydrate is an additional cortisol blocker that, when combined with pyruvate, produces a synergistic effect in increasing the lean body mass of a mammal. The combination of pyruvate and creatine monohydrate also produces an increase in the athletic performance of the mammal by enhancing the energy level of the mammal.

Pregnenalone, a prohormone like DHEA, is a substance which the body utilizes to synthesize various hormones that regulate metabolism. Pregnenalone is known as a fat controlling agent and a lean tissue builder. Campbell reported in the *Journal of Endocrinology*, 94(2), 1982, pages 225–242, that exogenous pregnenalone increases the production of the anabolic steroid aldosterone while not increasing the production of the catabolic steroid corticosterone.

The present invention is based in part, upon the discovery that the use of pyruvate in enteral formulations, in combination with a cortisol blocker, such as phosphatidylserine, HMB, DHEA, CLA , creatine monohydrate, pregnenalone and the like, produces a synergistic effect in increasing the lean body mass or muscle tissue of a mammal consuming same. The synergistic compositions of the present invention will also have a very beneficial impact on treating the catabolic conditions associated with diseases such as AIDS and cancer.

As used herein and in the claims, the term "pyruvate" means any salt or ester of pyruvic acid. Pyruvic acid has the formula:

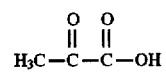

Pyruvic acid is a colorless liquid with an odor resembling that of acetic acid and has a melting point of 13° C. Pyruvic acid is an intermediate in the breakdown of sugars to alcohol by yeast. The mineral salts of pyruvic acid, such as magnesium pyruvate, potassium pyruvate, calcium pyruvate or mixtures thereof are useful in the present invention. Sodium pyruvate is not especially preferred as it is known that sodium is associated with various negative medical conditions such as high blood pressure, water retention and heart disease. Further, certain athletes such as bodybuilders and gymnasts desire to present a defined visual image of their body which shows muscle definition and thus, the water retention properties of the sodium salt are not beneficial. Pyruvate precursors in the form of pyruvamides or pyruvyl-amino acids are also useful in the present invention. Pyruvyl-glycine is representative of the useful pyruvyl-amino acids. Another pyruvate precursor is pyruvyl-creatine.

Pyruvate has a number of useful applications in medicine. Pyruvate has been described for retarding fatty deposits in livers (U.S. Pat. No. 4,158,057); for treating diabetes (U.S. Pat. No. 4,874,790); for retarding weight gain (U.S. Pat. Nos. 4,812,879, 4,548,937, and 4,351,835); to increase body protein concentrations in a mammal (U.S. Pat. No. 4,415,576); for treating cardiac patients to increase the cardiac output without accompanying increase in cardiac oxygen demand (U.S. Pat. No. 5,294,641); for extending athletic endurance (U.S. Pat. No. 4,315,835); for treating a hyperlipidemic animals (U.S. Pat. No. 5,134,162); for inhibiting growth and spread of malignancy and retarding DNA breaks (U.S. Pat. No. 5,612,374; and for inhibiting generation of free radicals (U.S. Pat. No. 5,480,909. All of these references are incorporated herein by reference.

Pyruvate in various forms has been proposed for enteral administration and for parenteral administration. Typically, pyruvates are available in the form of salts, for example, calcium pyruvate and magnesium pyruvate. U.S. Pat. Nos. 5,283,260 and 5,256,697 disclose uses for the pyruvyl-amino acids and methods for their production.

Pyruvate has been administered to mammals enterally or parenterally typically at superphysiological levels. The amount of pyruvate administered, generally ranges from 1 to 20% of the mammal's caloric intake. For enteral dosage, the pyruvate may be disbursed or dissolved in a beverage product or may be included in cookies, candies or other foods. Pyruvate may also be introduced as an aqueous solution parenterally.

DISCLOSURE OF THE INVENTION

There is disclosed an enteral composition comprising pyruvate and a cortisol blocker. There is further disclosed a composition wherein the cortisol blocker is selected from the group consisting of phosphatidylserine, HMB, DHEA, CLA, anabolic steroids, creatine monohydrate, pregnenalone and Ipriflavone. Representative of the anabolic steroids useful in the present invention is androstenedione. Other forms of creatine such as creatine-amino acid adducts are also useful. Further, pyruvyl-creatine is a useful composition.

Additional cortisol blockers useful in the present invention include high levels of leucine, antioxidants such as vitamin E and β-carotene, leucine metabolites, and glutamic acid derivatives and their metabolites. Representative of a glutamic acid metabolite useful in the present invention is glutamine. As used herein and in the claims, the term cortisol blocker means any known compound that blocks, inhibits, retards or prevents the catabolic breakdown of muscle tissue that results from strenuous exercise or diseases such as cancer and AIDS.

There is further disclosed a method for increasing the lean body mass or muscle mass of a mammal, said process comprising administering to a mammal in need of increased lean body mass or muscle mass, a composition comprising pyruvate and a cortisol blocker. The weight ratio of pyruvate to cortisol blocker can range from 1:20 to 20:1. More preferably, the weight ratio of pyruvate to cortisol blocker is 1:5 to 5:1. The amount of the pyruvate and cortisol blocker composition administered to the mammal ranges from 1 to 100 gms per day. More preferred, the mammal should consume from 5 to 50 gms per day. On a weight to weight basis, the animal should consume from 0.01 to 1.0 gms per kg of body weight per day of the inventive composition. More specifically, a typical adult human (body weight of 75 kgs) should be administered at least 3 gms of pyruvate (based on weight of the pyruvate anion and not the mineral cation such as calcium) and at least 0.1 gms of the cortisol blocker.

The present invention also relates to a method for treating the catabolic effects of diseases such as cancer and AIDS through the administration of pyruvate and a cortisol blocker.

The invention is also concerned with a method for enhancing the physical endurance of a mammal, enhancing the athletic performance, increasing the lean body mass of a mammal and decreasing the deposition of body fat. The method comprises the administration of pyruvate to said mammal.

Specific forms of pyruvate useful in the present invention include magnesium pyruvate, calcium pyruvate, potassium pyruvate, pyruvyl-creatine pyruvyl-glycine, pyruvamines, pyruvyl-alanine, pyruvyl-leucine, pyruvyl-valine, pyruvyl-isoleucine, pyruvyl-phenylalanine, pyruvyl-proline, pyruvyl-sarcosine, their amides, esters and salts, and mixtures thereof.

The composition of the present invention may include other materials such as protein, fats, carbohydrates, vitamins, minerals, sweeteners, flavoring agents and the like. For example, the synergistic composition of the present invention, pyruvate plus cortisol blocker, may be combined with known food ingredients or dispersed in a liquid such as orange juice, and consumed orally. The synergistic composition of the present invention may also be in the form of a powder, liquids, tablet, capsule, pill, candy, confection, food additive or gel caps.

As used herein and in the claims, the term "food additive" means that the inventive composition is in a physical form that allows for its addition to a conventional foodstuff such as a pancake mix.

In the method of the present invention, the mammal, preferably a human, consumes at least 5 gms per day of the pyruvate/cortisol blocker composition. On a percent of calories basis, the synergistic combination cam comprise from 1 to about 20% of total caloric intake.

In a preferred embodiment, the inventive composition comprises the pyruvate in the form of calcium, potassium or magnesium pyruvate or mixtures thereof and at least one cortisol blocker selected from phosphatidylserine, HMB, DHEA, CLA, creatine monohydrate, pregnenalone, Ipriflavone, super physiological levels of leucine, anabolic steroids, such as androstenedione antioxidants, leucine metabolites, glutamic acid and its metabolites, and any compound demonstrated to possess the ability to block or lessen the catabolic effect of strenuous exercise. In a most preferred embodiment, the cortisol blocker is phosphatidylserine.

Phosphatidylserine is commercially available from Lucas Meyer, Inc. of Decatur, Ill. in the form of powders or fluids. Corti-PS™ 30P is a specifically processed soy lecithin powder made especially for encapsulated, tabletted and powdered nutritional supplements. Corti-PS™ 30P has the following composition:

| Composition per 100 grams | |
|---|---|
| Phospholipids | |
| Phosphatidylserine | 30% |
| Phosphatidylcholine | 15% |
| Phosphatidylethanolamine | 13% |
| Phosphatidylinositol | 6% |
| Fatty Acids | |
| Polyunsaturated | 33% |
| Monounsaturated | 5% |
| Saturated | 12% |

In the practice of the present invention, the level of the phosphatidylserine in the starting materials should be as high as possible as the other components found in commercially available sources of phosphatidylserine increase the volume of material to be consumed or may be antagonistic to the beneficial properties of the inventive composition.

The present invention also contemplates the separate oral administration of the pyruvate and the cortisol blocker. Therefore, dosages of each component can occur separately, provided both components are found systematically in the mammal prior to strenuous exercise.

In order to demonstrate the present invention, the following example is submitted.

EXAMPLE I

Three groups of 10 rats (Control, Control Pyruvate and Control Cortisol Blocker), each weighing about 200 gms, are fed a standard laboratory diet supplemented as described below, for a period of 60 days. The standard rat diet contains 15% protein, 28% fat and 57% carbohydrate. A fourth group of 10 rats (Experimental) is fed the same standard diet as the Controls, except for the addition of a mixture of sodium pyruvate, calcium pyruvate and Corti-PS™ 30P (phosphatidylserine) powder from Lucas Meyer, Inc. of Decatur, Ill. The mixture is 80% by wt. calcium pyruvate, and 20% by wt. Corti-PS™ 30P which provides 6 wt. % of the total mixture as phosphatidylserine. The weight ratio of pyruvate to phosphatidylserine is thus 50:6 or 8.33 to 1. The Experimental group diet is a 90 wt. % blend of the standard diet with 10 wt. % of the inventive mixture. The Control diet is iso-energetically supplemented with maltose-dextrine and the electrolyte composition of the Control diet is made equal to the Experimental diet by adding appropriate amounts of calcium carbonate and sodium citrate. The Control Pyruvate diet contains the same amount of pyruvate as the Experimental and was iso-energetically supplemented with maltose-dextrine to account for the missing phosphatidylserine. The Control Cortisol Blocker diet contains the same level of phosphatidylserine as the Experimental and is iso-energetically supplemented with maltose-dextrine, calcium carbonate and sodium citrate to account for the missing pyruvate. Over the 60 day feeding period, energy intake of the Experimental and Control groups is about 250 calories per day.

Data on diet consumption per day is collected and the animals are also weighed daily. On days 7, 21, 39 and 60, post feeding, the rats are evaluated for total body fat using the water tank method as known to those skilled in the art. On day 7 post feeding, each rat is placed in an exercise cage driven by an electric motor. The speed of the exercise cage is set at 100 rpm. The time for each rat to fail to keep up with the set speed is measured. Failure to meet the set speed of the wheel is determined when the rat becomes inverted within the cage. The time to failure is a measure of endurance of the rat and simulates strenuous exercise in the human. This procedure of exercise to exhaustion is performed daily except for days 14, 21, 28, 35, 39, 46, 53 and 60.

The exercise cage data will indicate that the average time to exhaustion of the Experimental group is 30% greater that the Control and Control Cortisol Blocker groups. The Control Pyruvate rats will demonstrate a 10% longer time to exhaustion that the Control and Control Cortisol Blocker rats. This is evidence that this inventive, synergistic composition increases endurance and/or performance in an mammal.

The total body fat data will indicate that the Experimental group has a 15% increase in lean body tissue (muscle) over all the Controls. The data will also indicate that the Experimental group gained 20% less fat than the Control and Control Cortisol Blocker groups.

There will be found a marked increase of protein concentration (muscle tissue) in the animals fed the composition of the present invention. The synergistic effect of the present invention provides for an increase in body protein concentration by blocking the catabolic effects of cortisol on muscle tissue while decreasing the deposition of body fat.

An additional important indicator of the novel synergistic composition's effectiveness has been a significant lowering of the perceived difficulty of long term exercise among individuals that consume the pyruvate/cortisol blocker composition. The lower difficulty perceived by individuals receiving the pyruvate/cortisol blocker composition of the invention will lead to enhanced physical performance, especially when long term exercise, such as marathons, are involved.

In a preferred embodiment of the present invention, there is provided a container or package containing a pharmaceutically acceptable mixture of pyruvate and phosphatidylserine in a unit dosage quantity (i.e., pills or capsules) together with instructions for administration of effective quantities over a period of time. In another embodiment, the synergistic composition of this invention is in combination with a liquid or powdered base, such as milk, glucose, protein, flavoring agents or carbohydrates, to improve patient acceptance of the composition. The composition of this invention may also be incorporated as an ingredient in a foodstuff such as cookies, pretzels, candies, chewing gums, rehydration solutions and the like.

Industrial Applicability

The medical community and the serious athlete are constantly searching for compositions and methods that will enhance athletic performance and/or endurance while also increasing the lean body mass, protein concentration and muscle mass of the athlete. There is also a need for nutritional compositions that will assist the catabolic patient (i.e., cancer and AIDS) in maintaining weight or preventing further weight loss. There is also a need for compositions which reduce the deposition of body fat and reduce the catabolic effects of strenuous exercise. The present invention is based in part on the synergistic combination of two known chemical entities which surprisingly produce outstanding increases in athletic endurance and performance while also increasing body protein concentration and muscle mass while lessening the deposition of fat in the body. The present invention will be of substantial benefit to all athletes, especially bodybuilders, weight lifters, football players and the like.

Although the invention has been described in connection with certain specific embodiments, it will be readily apparent to those skilled in the art that various changes can be made to suit specific requirements without departing from the spirit of and scope of the invention.

I claim as my invention:

1. A composition for enteral administration comprising pyruvate and a cortisol blocker.

2. A composition according to claim 1 wherein said pyruvate is selected from the group comprising sodium pyruvate, calcium pyruvate, magnesium pyruvate, potassium pyruvate, pyruvyl-creatine, pyruvyl-glycine, pyruvamides, pyruvyl-alanine, pyruvyl-leucine, pyruvyl-valine, pyruvyl-isoleucine, pyruvyl-phenylalanine, pyruvyl-proline, pyruvyl-sarcosine, their amides, esters and salts and mixtures thereof.

3. A composition according to claim 2 wherein said pyruvate is selected from the group consisting of calcium pyruvate, magnesium pyruvate, potassium pyruvate and mixtures thereof.

4. A composition according to claim 1 wherein said cortisol blocker is selected from the group consisting of phosphatidylserine, HMB, DHEA, CLA, anabolic steroids, creatine monohydrate, pregnenalone, Ipriflavone, super physiological levels of leucine, anabolic steroids, antioxidants, leucine metabolites, glutamic acid and its metabolites, glutamine and androstenedione.

5. A composition according to claim 1 wherein the weight ratio of pyruvate to cortisol blocker can range from 1:20 to 20:1.

6. A composition according to claim 1 wherein said composition is in the form of powder, liquid, tablet, capsule, pill, candy, confection food additive or gel cap.

7. A method for increasing the protein concentration, lean body mass or muscle mass in a mammal which comprises administering orally to a mammal in need thereof, a therapeutically effective amount of pyruvate and a cortisol blocker.

8. A method according to claim 7 wherein said pyruvate is selected from sodium pyruvate, calcium pyruvate and mixtures thereof, and wherein said cortisol blocker is phosphatidylserine, and wherein said pyruvate and phosphatidylserine are in a weight ratio of 3:1 to 1:3 and wherein said mammal is administered from 5 to 100 gms of the pyruvate/phosphatidylserine mixture per day.

9. A method according to claim 7 wherein said pyruvate is selected from the group comprising of sodium pyruvate, calcium pyruvate, magnesium pyruvate, potassium pyruvate, pyruvyl-creatine, pyruvyl-glycine, pyruvamides, pyruvyl-alanine, pyruvyl-leucine, pyruvyl-valine, pyruvyl-isoleucine, pyruvyl-phenylalanine, pyruvyl-proline, pyruvyl-sarcosine, their amides, esters and salts and mixtures thereof.

10. A method according to claim 7 wherein said cortisol blocker is selected from the group consisting of phosphatidylserine, HMB, DHEA, CLA, anabolic steroids, creatine monohydrate, pregnenalone, Ipriflavone, super physiological levels of leucine, anabolic steroids, antioxidants, leucine metabolites, glutamic acid and its metabolites, glutamine and androstenedione.

11. A method according to claim 7 wherein said pyruvate is selected from the group consisting of calcium pyruvate, magnesium pyruvate, potassium pyruvate and mixtures thereof.

12. A method according to claim 7 wherein the weight ratio of pyruvate to cortisol blocker can range from 1:20 to 20:1.

13. A method according to claim 7 wherein the pyruvate and cortisol blocker are in admixture and are in the form of a powder, tablet, liquid, capsule, pill, candy, confection, food additive or gel cap.

14. A method for increasing the lean body mass of a mammal and decreasing the deposition of fat, said method comprising enteral administration of pyruvate to said mammal.

* * * * *